US012672867B2

(12) United States Patent
McClellan et al.

(10) Patent No.: US 12,672,867 B2
(45) Date of Patent: Jul. 7, 2026

(54) ALL-SUTURE ANCHOR, INSTRUMENTS, AND METHODS OF USING THE SAME

(71) Applicant: MedShape, Inc., Atlanta, GA (US)

(72) Inventors: Ian Perry McClellan, Lawrenceville, GA (US); Courtney Lynne Kline, Sandy Springs, GA (US)

(73) Assignee: MEDSHAPE, INC., Atlanta, GA (US)

( * ) Notice: Subject to any disclaimer, the term of this patent is extended or adjusted under 35 U.S.C. 154(b) by 61 days.

(21) Appl. No.: 18/940,438

(22) Filed: Nov. 7, 2024

(65) Prior Publication Data

US 2025/0143689 A1 May 8, 2025

Related U.S. Application Data

(60) Provisional application No. 63/596,864, filed on Nov. 7, 2023.

(51) Int. Cl.
*A61B 17/04* (2006.01)

(52) U.S. Cl.
CPC ...... *A61B 17/0401* (2013.01); *A61B 17/0485* (2013.01); *A61B 2017/0414* (2013.01)

(58) Field of Classification Search
CPC ............ A61B 17/0401; A61B 17/0485; A61B 2017/0409; A61B 2017/0406; A61B 2017/0414; A61B 2017/0477; A61B 2017/0496
USPC ........................................................ 606/228
See application file for complete search history.

(56) References Cited

U.S. PATENT DOCUMENTS

| | | | |
|---|---|---|---|
| D24,855 | S | 11/1895 | Trapp |
| 4,884,572 | A | 12/1989 | Bays et al. |
| 4,898,456 | A | 2/1990 | Gatturna et al. |
| 5,013,316 | A | 5/1991 | Goble et al. |
| 5,100,417 | A | 3/1992 | Cerier et al. |
| D330,591 | S | 10/1992 | Rosenberg et al. |
| D331,463 | S | 12/1992 | Rosenberg et al. |
| 5,224,946 | A | 7/1993 | Hayhurst et al. |
| 5,258,016 | A | 11/1993 | Dipoto et al. |
| 5,370,662 | A | 12/1994 | Stone et al. |
| 5,411,506 | A | 5/1995 | Goble et al. |
| 5,486,197 | A | 1/1996 | Le et al. |
| 5,545,180 | A | 8/1996 | Le et al. |
| 5,584,860 | A | 12/1996 | Goble et al. |
| D386,583 | S | 11/1997 | Ferragamo et al. |
| 5,707,395 | A | 1/1998 | Li |

(Continued)

*Primary Examiner* — Jocelin C Tanner
(74) *Attorney, Agent, or Firm* — Husch Blackwell LLP; Bryan D. Stewart

(57) ABSTRACT

The present disclosure relates to a suture anchor assembly that includes a sleeve having an elongated configuration and a tightened configuration. The suture anchor includes a first deployment strand and a second deployment strand that each form a looped end and a free end. The free end of the first deployment strand passes through the looped end of the second deployment strand and the free end of the second deployment strand passes through the looped end of the first deployment strand to form a loose square knot. A portion of the first deployment strand and the second deployment strand pass through the sleeve. Application of tension to each of the free end of the first deployment strand and the free end of the second deployment strand causes the loose square knot to tighten and the sleeve to move to the tightened configuration.

20 Claims, 4 Drawing Sheets

(56)                References Cited

U.S. PATENT DOCUMENTS

| | | | |
|---|---|---|---|
| 5,725,557 A | 3/1998 | Gatturna et al. | |
| 5,741,300 A | 4/1998 | Li | |
| 5,868,789 A | 2/1999 | Huebner | |
| 5,957,924 A | 9/1999 | Tormala et al. | |
| 5,961,524 A | 10/1999 | Crombie | |
| 5,989,252 A * | 11/1999 | Fumex | A61B 17/0401 |
| | | | 606/232 |
| 5,993,459 A | 11/1999 | Larsen et al. | |
| 6,165,203 A | 12/2000 | Krebs | |
| 6,168,598 B1 | 1/2001 | Martello | |
| 6,283,973 B1 | 9/2001 | Hubbard et al. | |
| 6,527,777 B2 | 3/2003 | Justin | |
| 6,916,323 B2 | 7/2005 | Kitchens | |
| 6,989,014 B2 | 1/2006 | Justin et al. | |
| 7,189,238 B2 | 3/2007 | Lombardo et al. | |
| 7,220,266 B2 | 5/2007 | Gambale | |
| 7,517,357 B2 | 4/2009 | Abrams et al. | |
| D605,763 S | 12/2009 | Griffis, III et al. | |
| 7,641,672 B2 | 1/2010 | Fallin et al. | |
| 7,713,286 B2 | 5/2010 | Singhatat | |
| 7,749,250 B2 * | 7/2010 | Stone | A61B 17/0482 |
| | | | 606/232 |
| 7,780,701 B1 | 8/2010 | Meridew et al. | |
| D625,816 S | 10/2010 | Griffis, III et al. | |
| 7,905,904 B2 * | 3/2011 | Stone | A61B 17/0469 |
| | | | 606/232 |
| 7,959,650 B2 | 6/2011 | Kaiser | |
| 8,048,158 B2 | 11/2011 | Hays et al. | |
| 8,062,334 B2 | 11/2011 | Green et al. | |
| 8,128,658 B2 | 3/2012 | Kaiser | |
| D657,872 S | 4/2012 | Griffis et al. | |
| D665,078 S | 8/2012 | Griffis et al. | |
| 8,317,825 B2 | 11/2012 | Stone | |
| 8,679,168 B2 | 3/2014 | McNamara et al. | |
| 9,173,652 B2 | 11/2015 | Lombardo | |
| 9,402,621 B2 | 8/2016 | Stone | |
| 9,463,011 B2 | 10/2016 | Dreyfuss | |
| 9,622,738 B2 | 4/2017 | Dreyfuss | |
| 9,622,740 B2 | 4/2017 | Nason | |
| 9,737,292 B2 | 8/2017 | Sullivan | |
| 9,820,731 B2 | 11/2017 | Arai | |
| 9,826,971 B2 | 11/2017 | Lombardo | |
| 9,867,607 B2 | 1/2018 | Sullivan | |
| 10,517,587 B2 | 12/2019 | Denham | |
| 10,595,845 B2 | 3/2020 | Burkhart | |
| 11,006,945 B2 | 5/2021 | Pilgeram | |
| 2007/0198017 A1 | 8/2007 | Tschakaloff | |
| 2008/0071278 A1 | 3/2008 | Assell et al. | |
| 2008/0109037 A1 | 5/2008 | Steiner et al. | |
| 2008/0234731 A1 | 9/2008 | Leung et al. | |
| 2009/0143809 A1 | 6/2009 | Assell et al. | |
| 2009/0163963 A1 | 6/2009 | Berrevoets | |
| 2009/0287226 A1 | 11/2009 | Gellman et al. | |
| 2009/0292313 A1 | 11/2009 | Anspach, III et al. | |
| 2010/0016902 A1 | 1/2010 | Paulk et al. | |
| 2010/0063542 A1 | 3/2010 | Van Der Burg et al. | |
| 2010/0121348 A1 | 5/2010 | Van Der Burg et al. | |
| 2010/0179592 A1 | 7/2010 | Martinek et al. | |
| 2010/0198258 A1 | 8/2010 | Heaven | |
| 2010/0292733 A1 | 11/2010 | Hendricksen et al. | |
| 2010/0331881 A1 | 12/2010 | Hart | |
| 2015/0250471 A1 | 9/2015 | Nason | |
| 2016/0051246 A1 | 2/2016 | Durando | |
| 2020/0138429 A1 | 5/2020 | Dreyfuss | |
| 2021/0353280 A1 | 11/2021 | Black | |

* cited by examiner

600

602 — Create Pilot Hole in Bone

604 — Push Anchor into Bone

606 — Deploy Anchor by Tensioning Free Ends

608 — Remove Insertion Tool

ALL-SUTURE ANCHOR, INSTRUMENTS, AND METHODS OF USING THE SAME

CROSS-REFERENCE TO RELATED APPLICATION

This application claims priority to U.S. Provisional Patent Application No. 63/596,864, filed on Nov. 7, 2023, and titled "ALL-SUTURE ANCHOR, INSTRUMENTS, AND METHODS OF USING THE SAME," the contents of which are incorporated herein by reference in their entirety

TECHNICAL FIELD

In various embodiments, the present disclosure relates to suture anchors, related instrumentation, and methods of using suture anchors and instruments.

BACKGROUND

In various surgical procedures, suturing techniques aid in stabilizing soft tissues and ensuring proper alignment of an implant. Devices such as suture anchors provide fixation in bone, allowing a surgeon to securely attach sutures. Many suture anchors today include additional hardware to anchor a suture to bone, such as, for example, an expandable post that attaches to a suture. Additional hardware can add surgical procedure complexity, time, and expense.

Suture anchors that do not include additional hardware typically require sustained tension on the sutures to hold a knot. Sustained tension can be challenging for surgeons as they use the sutures (at the opposite end as the knot) to suture a ligament or other soft tissue structure.

BRIEF SUMMARY OF THE DISCLOSURE

There is a need for an all-suture anchor that does not require sustained tension. In various embodiments, the present suture anchor assembly includes a knot construct (e.g., a square knot or reef knot) that allows one or more strands to slide while still maintaining the knot, and where the soft suture anchor remains deployed even after tension from the ends of the strands is released. Further, the present suture anchor construct requires less force to deploy, providing additional advantages over previous suture anchor technology.

As will be understood from discussions here, suture anchor devices and instruments may securely attach sutures to the bone, stabilizing soft tissues and ensuring proper alignment of a joint. Such suture anchors and insertion devices may allow for precise placement of the sutures, which improves soft tissue fixation and the success of an implant. Using a suturing tool may ensure the anchor is inserted at the correct depth and angle, provide for controlled tension on the suture, and reduces the risk of complications like anchor displacement or suture failure.

According to a first aspect of the present disclosure, a suture anchor assembly comprises: a sleeve having an elongated configuration and a tightened configuration; a first deployment strand and a second deployment strand, each of the first deployment strand and the second deployment strand forming a looped end and a free end, wherein: the free end of the first deployment strand passes through the looped end of the second deployment strand and the free end of the second deployment strand passes through the looped end of the first deployment strand, thereby forming a loose square knot with a first crossover and a second crossover; a portion of the first deployment strand and a portion of the second deployment strand pass through the sleeve; and application of tension to each of the free end of the first deployment strand and the free end of the second deployment strand causes the loose square knot to tighten and the sleeve to move to the tightened configuration.

According to a second aspect of the first aspect or any other aspect, wherein the first crossover comprises the portion of the first deployment strand and the portion of the second deployment strand that passes through the sleeve.

According to a third aspect of the first aspect or any other aspect, further comprising an insertion tool for inserting the suture anchor assembly into a pilot hole.

According to a fourth aspect of the third aspect or any other aspect, wherein the insertion tool further comprises a spool for storing excess suture material.

According to a fifth aspect of the third aspect or any other aspect, wherein the insertion tool comprises an insertion tool first end and an insertion tool second end, the insertion tool first end including a handle and the insertion tool second end including an elongated body configured to insert the suture anchor assembly into the pilot hole.

According to a sixth aspect of the fifth aspect or any other aspect, wherein the insertion tool second end comprises a flat end or a rounded end.

According to a seventh aspect of the fifth aspect or any other aspect, wherein the insertion tool second end comprises an anchor slot for receiving at least a portion of the suture anchor assembly.

According to an eighth aspect of the fourth aspect or any other aspect, wherein the insertion tool further comprises one or more eyelets positioned along a length of the elongated body.

According to a ninth aspect of the eighth aspect or any other aspect, wherein the one or more eyelets include a plurality of eyelets that are positioned at one or more predetermined lengths from the insertion tool second end to allow a surgeon to insert the suture anchor assembly at a controlled depth.

According to a tenth aspect of the first aspect or any other aspect, further comprising a drill for drilling a pilot hole into a bone.

According to a eleventh aspect of the first aspect or any other aspect, wherein one or more of the first deployment strand, the second deployment strand, and the sleeve are comprised of a material infused with osteoconductive material.

According to a twelfth aspect of the present disclosure, A method of attaching a suture anchor assembly to a bone, comprises drilling a pilot hole into the bone using a drill; inserting an anchor into the pilot hole via an insertion tool, the anchor comprising: a sleeve having an elongated configuration and a tightened configuration; a first deployment strand and a second deployment strand, each of the first deployment strand and the second deployment strand forming a looped end and a free end, wherein: the free end of the first deployment strand passes through the looped end of the second deployment strand and the free end of the second deployment strand passes through the looped end of the first deployment strand, thereby forming a loose square knot with a first crossover and a second crossover; and a portion of the first deployment strand and a portion of the second deployment strand pass through the sleeve; deploying the anchor by tensioning the free end of the first deployment strand and the free end of the second deployment strand, thereby tightening the square knot and causing the sleeve to move to the tightened configuration; and removing the insertion tool from the pilot hole.

According to a thirteenth aspect of the twelfth aspect or any other aspect, wherein the first crossover comprises the portion of the first deployment strand and the portion of the second deployment strand that passes through the sleeve.

According to a fourteenth aspect of the twelfth aspect or any other aspect, wherein one or more of the first deployment strand, the second deployment strand, and the sleeve are comprised of a material infused with osteoconductive material.

According to a fifteenth aspect of the twelfth aspect or any other aspect, further comprising inserting the suture anchor assembly into an anchor slot of the insertion tool.

According to a sixteenth aspect of the twelfth aspect or any other aspect, further comprising inserting the suture anchor assembly into an anchor slot of the insertion tool.

According to a seventeenth aspect of the twelfth aspect or any other aspect, further comprising inserting the suture anchor assembly into one or more eyelets of an elongated body of the insertion tool.

According to an eighteenth aspect of the seventeenth aspect or any other aspect, wherein the suture anchor assembly is inserted into a predetermined eyelet at a predetermined length from an end of the insertion tool to control an insertion depth.

According to a nineteenth aspect of the present disclosure, a kit for attaching a suture anchor assembly to a bone, comprises: a drill configured to drill a pilot hole into the bone; an insertion tool configured to insert a suture anchor assembly into the pilot hole; and the suture anchor assembly comprising: a sleeve including an elongated configuration and a tightened configuration; a first deployment strand and a second deployment strand, each of the first deployment strand and the second deployment strand forming a looped end and a free end, wherein: the free end of the first deployment strand passes through the looped end of the second deployment strand and the free end of the second deployment strand passes through the looped end of the first deployment strand, thereby forming a loose square knot with a first crossover and a second crossover; a portion of the first deployment strand and a portion of the second deployment strand pass through the sleeve; and application of tension to each of the free end of the first deployment strand and the free end of the second deployment strand causes the loose square knot to tighten and the sleeve to move to the tightened configuration.

According to a twentieth aspect of the nineteenth aspect or any other aspect, wherein the first crossover comprises the portion of the first deployment strand and the portion of the second deployment strand that passes through the sleeve.

BRIEF DESCRIPTION OF THE DRAWINGS

The foregoing Summary and the following Detailed Description will be better understood when read in conjunction with the appended drawings. In the drawings.

DETAILED DESCRIPTION

The following detailed description references specific embodiments in which the certain embodiments of the present disclosure can be practiced. The embodiments are intended to describe aspects of the present disclosure in sufficient detail to enable those skilled in the art to practice the same. Other embodiments can be utilized, and changes can be made without departing from the scope of the present disclosure. It will be appreciated that some or all the various features and structures described and shown with respect to each of the specific embodiments referenced herein may be combined to form additional or alternative embodiments having such combinations and that such combinations are within the scope of the present invention.

As discussed above, the present suture anchor device, instruments, and processes provide advantages over previous technology. First, in at least one embodiment, the present suture anchor assembly requires less force to secure a suture anchor. Second, in various embodiments, the present suture anchor assembly includes a knot construct (e.g., a square knot or reef knot) that allows one or more strands to slide while still maintaining the knot, and where the soft suture anchor remains deployed even after tension from the ends of the strands is released.

Figure 1:
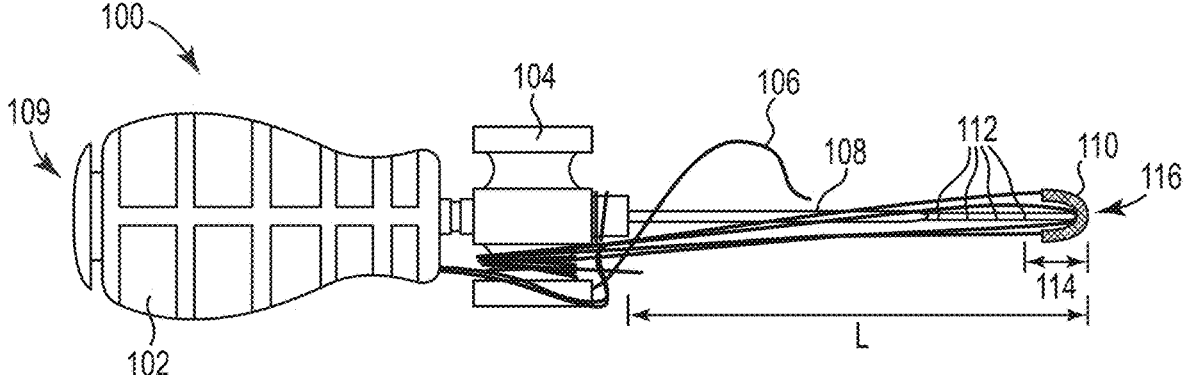
FIG. 1 is a front view of an insertion tool for inserting one or more suture anchor assemblies into a bone, in accordance with one or more embodiments of the present disclosure.

FIG. 1 is a front view of an insertion tool 100 for inserting one or more suture anchor assemblies into a bone, in accordance with one or more embodiments of the present disclosure. In certain embodiments, and as shown in FIG. 1, the insertion tool 100 includes a handle 102, a spool 104, suture material 106, an elongated body 108, a first end 109, a second end 110, and one or more eyelets 112. In certain embodiments, the second end 110 includes a flat or rounded end. The second end 110 can include an anchor slot 116 for receiving at least a portion of a suture anchor assembly 200 (as illustrated and described in further detail with respect to FIGS. 3-4).

In certain embodiments, the handle 102 is ergonomically designed to provide a comfortable grip for the surgeon, allowing for precise control during the suturing process. Furthermore, the handle 102 can include one or more features like a textured surface or finger grooves to enhance stability and reduce the risk of slipping, ensuring accurate placement of sutures during delicate procedures.

In various embodiment, the spool 104 is configured to store excess suture material 106. This may allow for smooth and controlled unwinding of the suture material 106 as the surgeon determines and uses various lengths of the suture material 106. As shown in FIG. 1 the design of the spool 104 enables the suture material 106 to unwind from the spool

104 as the surgeon ties one or more sutures while remaining tangle-free and easily accessible. Thus, the use of the spool 104 may facilitate efficient stitching while minimizing interruptions during the procedure. In at least one embodiment, the insertion tool 100 may include a spool with two sides or more than one spool.

In certain embodiments, the elongated body 108 connects the anchor slot 116 to the spool 104 and/or the handle 102. As will be understood, the elongated body 108 is configured to be inserted into a pilot hole that is drilled into a bone when a surgeon is placing a suture anchor assembly 200.

In certain embodiments, the elongated body 108 has an eyelet 112 or a plurality of eyelets 112 (as shown in FIG. 1) positioned along a length L of the elongated body 108. Alternately, the eyelet 112 or plurality of eyelets 112 may be a plurality of markers for gauging depth of the elongate body 108 (e.g., how deep the suture anchor assembly 200 is placed within bone). In certain embodiments, the plurality of eyelets 112 are positioned at one or more predetermined lengths 114 from the insertion tool second end 110 to allow a surgeon to insert the suture anchor assembly at a controlled depth. In certain embodiments, the plurality of eyelets 112 can be evenly spaced apart from one another to allow for a surgeon to easily determine changes in depth from one eyelet 112 to another.

In various embodiments, the eyelets 112 are configured to facilitate the threading of the suture material 106 through the elongated body 108 of the insertion tool 100. According to particular embodiments, the eyelets 112 serve as a small hole or loop through which the suture thread is passed, allowing the needle to carry the suture material 106 to a desired location during the suturing process. This design may help in securely anchoring the suture material 106.

Figure 2:
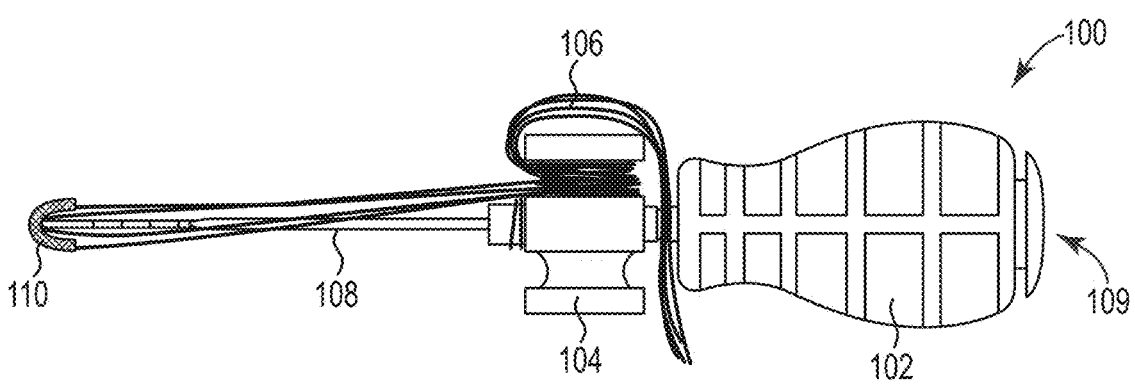
FIG. 2 is a rear view of the insertion tool of FIG. 1 for inserting one or more suture anchor assemblies into a bone, in accordance with one or more embodiments of the present disclosure.

FIG. 2 is a rear view of the insertion tool 100 of FIG. 1 for inserting one or more suture anchor assemblies into a bone, in accordance with one or more embodiments of the present disclosure. The insertion tool 100 as shown in FIG. 2 includes certain similar components as discussed in FIG. 1, including the handle 102, the spool 104, the suture material 106, the first end 109, and the second end 110.

Figure 3:
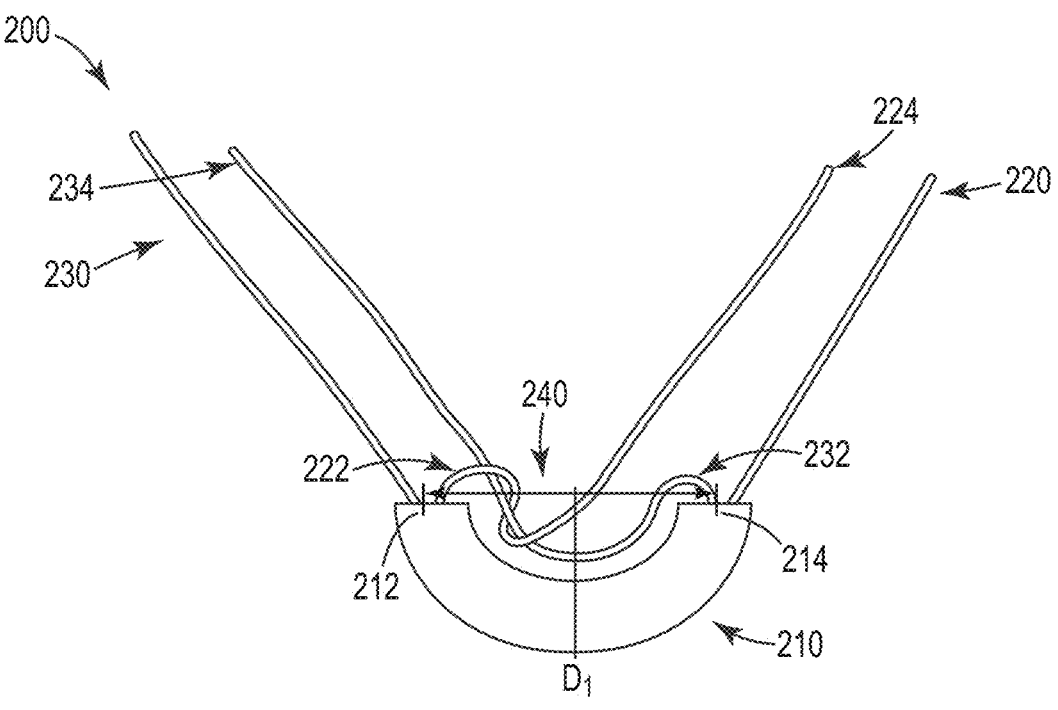
FIG. 3 is a suture anchor assembly arranged in an elongated configuration, in accordance with one or more embodiments of the present disclosure.

FIG. 3 is a suture anchor assembly 200 arranged in an elongated configuration, in accordance with one or more embodiments of the present disclosure. In certain examples, and as shown in FIG. 3 by non-limiting example, the suture anchor assembly 200 can include a sleeve 210, a first deployment strand 220, a first deployment strand looped end 222, a first deployment strand free end 224, a second deployment strand 230, a second deployment strand looped end 232, a second deployment strand free end 234, and a first crossover 240.

The sleeve 210 may form any useful shape and be composed of a biocompatible polymer (e.g., polypropylene, polyglycolic acid, polyglactin, polylactic acid, polycaprolactone, polyethylene, silicone, polyvinyl alcohol, or the like). In some embodiments, the sleeve 210 may be made of a flexible biocompatible material. Furthermore, the sleeve 210 may be shaped as a mesh tube or a coil structure.

As shown in FIG. 3, the sleeve may be a flexible tube. In other embodiments, the sleeve 210 may be shaped in a solid polymer tube with pores or slits, the sleeve 210 may be made of a solid material with no mesh or pores, and/or the sleeve 210 may be shaped in a flat rectangular shape instead of a tube. Further yet, the sleeve 210 may contain other features along an outermost surface to increase friction within a pilot hole of bone (e.g., pebbles, dimples, and/or bumps). In some embodiments, the sleeve 210 is comprised of a rough material which increases friction within the pilot hole.

Figure 6:
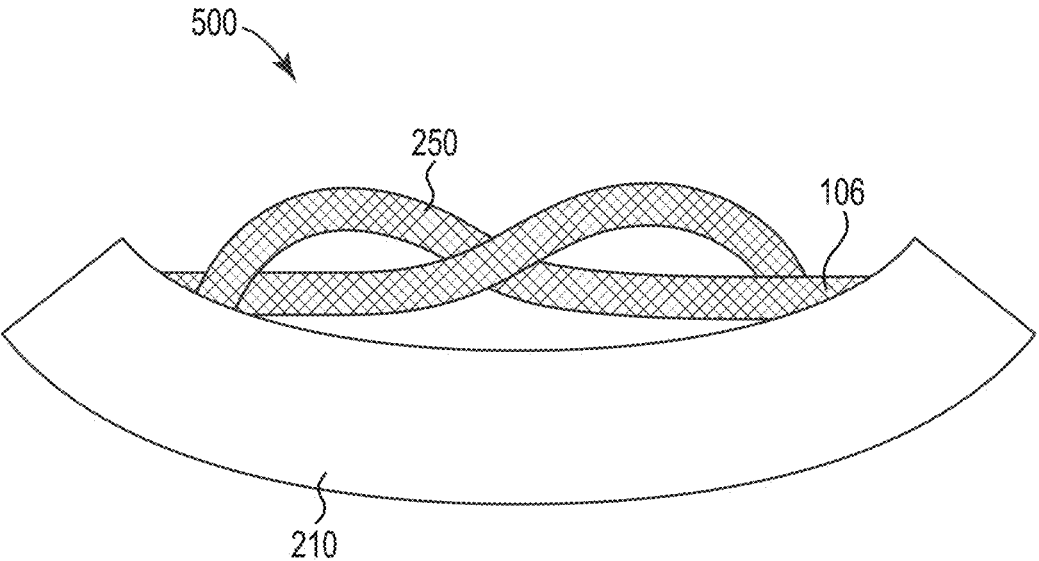
FIG. 6 is the suture of FIG. 5 tied into a square knot having a sleeve positioned over at least a portion of the square knot.

The first deployment strand 220 is shown having a first deployment strand looped end 222 and a first deployment strand free end 224. Further, the second deployment strand 230 is shown having a second deployment strand looped end 232 and a second deployment strand free end 234. As shown in FIG. 3 by non-limiting example, at least a portion of the first deployment strand 220 and the second deployment strand 230 are contained within the sleeve 210. Further, the first deployment strand 222 and the second deployment strand 230 have form a first crossover 240. As shown in FIG. 6, the deployment strands 222, 230 form a second crossover within the sleeve 210. The first crossover 240 is used to create a portion of the knot (e.g., the square knot or reef not), which, as shown in FIG. 3 is loose. In one or more embodiments the knot may be a thief knot, figure eight knot, a double figure eight knot, a bowline knot, or a sheet bend knot.

In some embodiments, the deployment strands 220, 230 are sutures comprised of suture material 106. The suture material 106 can include a variety of materials such as threads, plastic, absorbable materials (e.g., polyglycolic acid, vicryl, polylactic acid, etc.), non-absorbable materials (e.g., polypropylene, nylon, polyester, silk, etc.), or other materials. In various embodiments, the sutures may be coated with a treatment such as a bactericidal or antimicrobial coating. Sutures may also be coated with a wax, dye, silicon, fluorocarbon, or any other coating that maintains suture strength in the body. In various embodiments, the first and second deployment strands 220, 230 or the sleeve 210 is comprised of a material infused with osteoconductive material. Osteoconductive materials may comprise, by non-limiting example, calcium phosphate ceramics including hydroxyapatite, tricalcium phosphate, calcium sulfate and bioactive glass-ceramics. In various embodiments, the first and second deployment strand strands 220, 230 or the sleeve 210 are comprised of a material infused with hydroxyapatite.

As shown in FIG. 3, the suture anchor assembly 200 is in the elongated configuration (i.e., the sleeve first end 212 and the sleeve second end 214 are spaced apart a first distance D1 that is less than a second distance D2 (not shown) when the knot is tightened and the sleeve first end 212 and the sleeve second end 214 are pulled closer together. The second distance D2 and the tightening of the suture anchor assembly into the tightened configuration are illustrated and described in further detail below with respect to FIG. 4.

Figure 4:
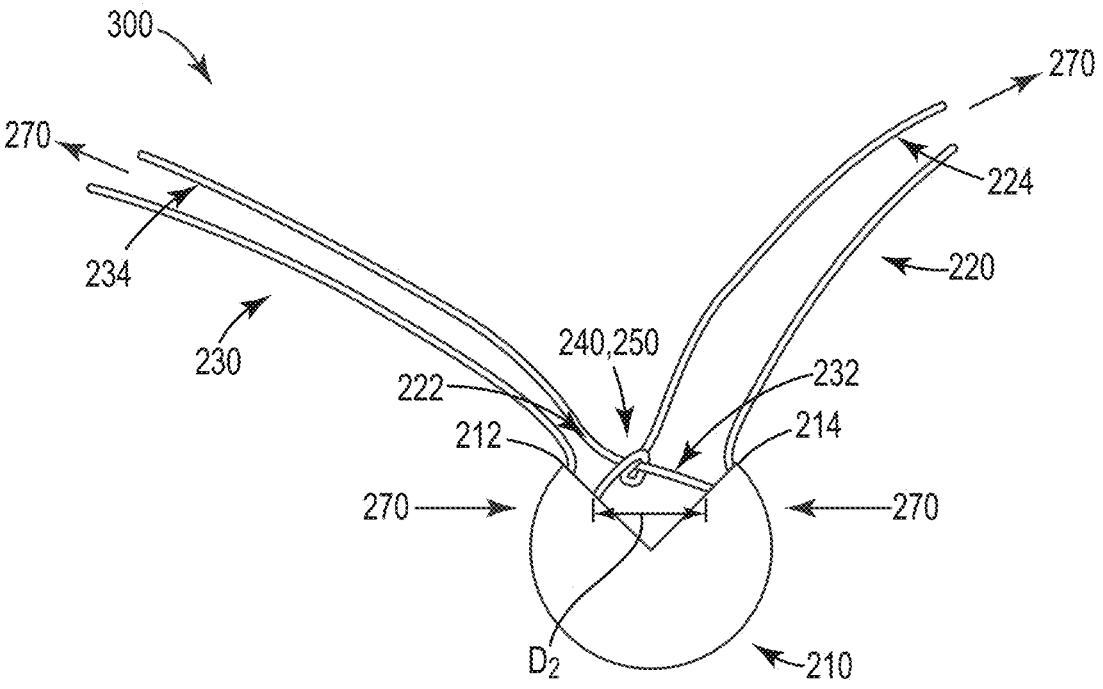
FIG. 4 is the suture anchor assembly of FIG. 3 arranged in a tightened configuration, in accordance with one or more embodiments of the present disclosure.

FIG. 4 is the suture anchor assembly 300 of FIG. 3 arranged in the tightened configuration, in accordance with one or more embodiments of the present disclosure. Several components of the suture anchor assembly 200 as shown in FIG. 4 are substantially similar to the components illustrated and described above with respect to FIG. 3, including the sleeve 210, a first deployment strand 220, a first deployment strand looped end 222, a first deployment strand free end 224, a second deployment strand 230, a second deployment strand looped end 232, a second deployment strand free end 234, and a first crossover 240.

As shown in FIG. 4 by non-limiting example, at least a portion of the first deployment strand 220 and the second deployment strand 230 are contained within the sleeve 210. Further, the first deployment strand 222 and the second deployment strand 230 have been looped together using a first crossover 240 and a second crossover 250 to form a square knot. As shown, the square knot is formed when the first deployment strand free end 224 passes through the second deployment strand looped end 232 and the second deployment strand free end 234 passes through the first deployment strand looped end 222. This creates the first crossover 240 and the second crossover 250, which form a loose square knot. The loose square knot is illustrated and described in further detail with respect to FIG. 6.

Continuing with FIG. 4, the suture anchor assembly 300 is at least partially in the tightened configuration (i.e., the sleeve first end 212 and the sleeve second end 214 are spaced apart a second distance D2 that is less than the first distance D1 as shown in FIG. 3 and the at least partially formed knot creates a semi-spherical bulge that presses against a pilot hole). The suture anchor assembly 300 transitions from the elongated configuration (as shown in FIG. 3) to the tightened configuration through application of tension (i.e., a tension force in a tension direction 270 where a surgeon may pull the deployment strands outward from the sleeve 210) to each of the first deployment strand free end 224 and the second deployment strand free end 234, which tightens the knot (e.g., the loose square knot) and pulls the sleeve first end 212 and the sleeve second end 214 closer together to decrease the first distance D1 to the second distance D2.

Figure 5:
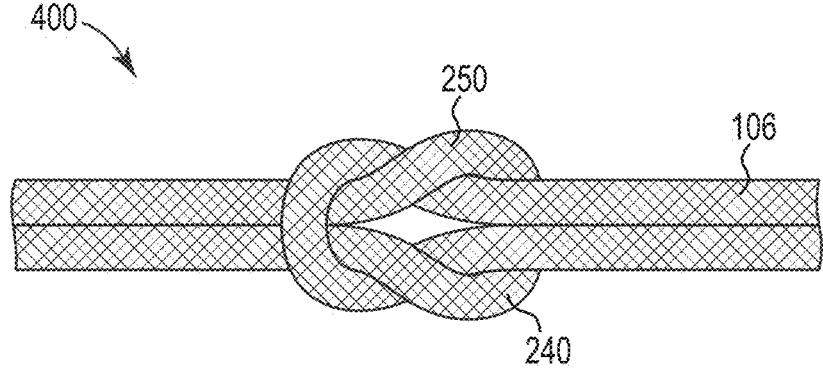
FIG. 5 is a suture that has been tied into a square knot (or reef knot), in accordance with one or more embodiments of the present disclosure.

FIG. 5 is a suture that has been tied into a square knot 400 (or reef knot), in accordance with one or more embodiments of the present disclosure. The square knot 400 is tied using suture material 106 to form the first crossover 240 and the second crossover 250. As shown in FIG. 5, the square knot 400 is tightened, which corresponds to the tightened position shown in FIG. 4.

FIG. 6 illustrates the suture of FIG. 5 tied into a loose square knot 500 having the sleeve 210 positioned over at least a portion of the square knot 400. The square knot 500 is tied using suture material 106 to form the first crossover 240 and the second crossover 250. As shown in FIG. 6, the square knot 500 is loose, which corresponds to the elongated position shown in FIG. 3.

Figure 7:
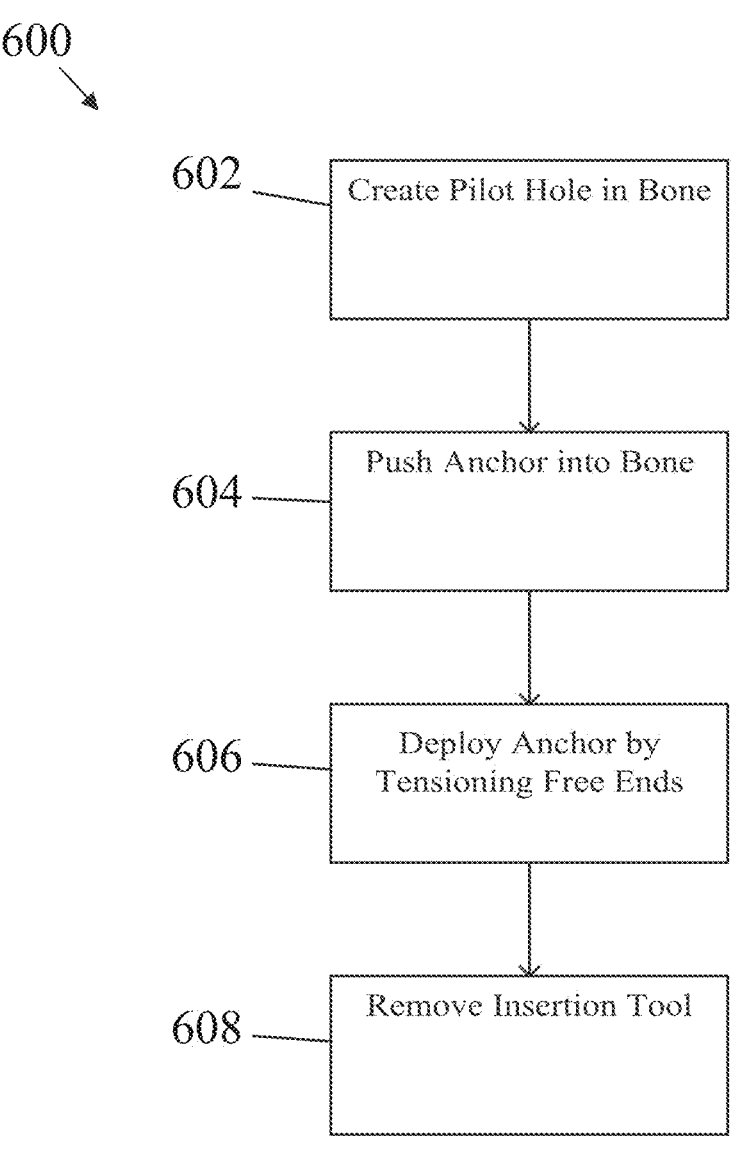
FIG. 7 is a method flow diagram of a method for inserting a suture anchor assembly into bone in an elongated position and activating the suture anchor assembly into a tightened configuration.

FIG. 7 is a method flow diagram of a method 600 for inserting a suture anchor assembly 200 into bone in an elongated position and activating the suture anchor assembly 200 into a tightened configuration.

The method 600 includes a step 602 of creating a pilot hole in bone. A process by which the pilot hole is drilled into the bone may include, by non-limiting example, identifying the placement site of the suture anchor assembly 200, preparing the bone surface to ensure good contact between the anchor and the bone, drilling into the bone to create a path for the suture anchor assembly 200, and confirming the depth and diameter of the pilot hole. The pilot hole can be drilled using a specialized drill bit such as a cannulated drill bit that is chosen to match the size of the suture anchor. Furthermore, when drilling the pilot hole at a predetermined site, a slight angle may be utilized to ensure optimal anchor placement.

The method 600 includes a step 604 of pushing (or inserting) the suture anchor assembly 200 into the bone. A process by which the suture anchor assembly 200 is inserted into the bone (i.e., into the pilot hole drilled into the bone) may include, by non-limiting example, a selection of an appropriate suture anchor material and design (e.g., deciding whether to use a bioresorbable polymer material, selecting a proper anchor size, deciding whether to use a self-tapping anchor, etc.), preparing the suture anchor assembly 200 (e.g., by preloading one or more sutures and threading them through the anchor before the insertion process begins), and inserting the suture anchor assembly 200 into the pilot hole using the insertion tool 100.

In various embodiments, the suture anchor assembly 200 may be pre-loaded on the insertion tool 100 and held in place via an anchor slot and tension in the deployment strands (loaded onto a spool or otherwise removable connected to a handle or elongate shaft). Stated differently, the suture anchor assembly 200 may be sold with the suture anchor assembly 200 removably attached to the insertion tool 100 so a surgeon may easily insert the suture anchor assembly 200 without loading the same on the insertion tool 100.

The method 600 includes a step 606 of deploying the suture anchor assembly 200 by tensioning the first deployment strand free end 224 and the second deployment strand free end 234 in a tensioning direction 270 (as illustrated and described in further detail with respect to FIG. 4).

The method 600 includes a step 608 of removing the insertion tool 100 from the patient.

As will be understood, the method 600 may include any number of additional steps, such as, but not limited to, determining a depth of the suture anchor assembly 200 (e.g., via the one or more eyelets or depth indicators 112), determining a length of one or more sutures (e.g., deployment strands 220, 230), unspooling a portion of the one or more sutures, trimming one or more sutures, performing additional suturing steps, such as, attaching the one or more sutures to soft tissue (e.g., a ligament) via a krackow or other stitching technique, etc.

Further, releasing the suture anchor assembly 200 may include releasing one or more sutures via the spool 104, trimming the one or more sutures, and tensioning the suture anchor assembly 200 (as discussed herein). In some embodiments, the insertion tool 100 may include a release mechanism for releasing the suture anchor assembly 200, such as, for example, a latch that releases upon pressing a button, an anchor slot that expands to release the suture anchor assembly 200, etc. Furthermore, in some embodiments, the insertion tool 100 can include a rotational control feature that allows for the anchor to be secured to the bone at a proper torque, a quick connect/disconnect feature for detaching the suture material 106 from the insertion tool 100, and a tactile feedback feature to indicate to a surgeon when the suture anchor assembly 200 is fully inserted in the correct position.

In certain embodiments, a kit for attaching a suture anchor assembly 200 to a bone can be assembled to perform one or more steps of the method 600. In certain embodiments, the kit can include an insertion tool 100 configured to insert the suture anchor assembly 200 into the pilot hole as illustrated and described above with respect to FIGS. 1, 2, and 7. Furthermore, in certain embodiments, the kit includes a drill configured to drill the pilot hole into the bone as illustrated and described in step 602. Further yet, the kit can include the suture anchor assembly 200, 300 as illustrated and described above with respect to FIGS. 3-6. Such a kit may include any other suitable instruments, such as a suture trimmer, nails, screws, stitch holders, needles, etc.

CONCLUSION

The foregoing description of the exemplary embodiments has been presented only for the purposes of illustration and description is not intended to be exhaustive or to limit the compositions, systems, and methods herein to the precise forms disclosed. Many modifications and variations are possible considering the above teachings.

The embodiments were chosen and described to explain the principles of the technology discussed herein and their practical application to enable others skilled in the art to utilize the various embodiments and with various modifications as are suited to the particular use contemplated. Alternative embodiments will become apparent to those skilled in the art to which the present technologies pertain without departing from their spirit and scope.

What is claimed is:

1. A suture anchor assembly comprising:

a sleeve having an elongated configuration and a tightened configuration;

a first deployment strand and a second deployment strand, each of the first deployment strand and the second deployment strand forming a looped end and a free end, wherein:

the free end of the first deployment strand passes through the looped end of the second deployment strand and the free end of the second deployment strand passes through the looped end of the first deployment strand, thereby forming a loose square knot with a first crossover and a second crossover;

a portion of the first deployment strand and a portion of the second deployment strand pass through the sleeve; and application of tension to each of the free end of the first deployment strand and the free end of the second deployment strand causes the loose square knot to tighten and the sleeve to move to the tightened configuration.

2. The suture anchor assembly of claim 1, wherein the first crossover comprises the portion of the first deployment strand and the portion of the second deployment strand that passes through the sleeve.

3. The suture anchor assembly of claim 1, further comprising an insertion tool for inserting the suture anchor assembly into a pilot hole.

4. The suture anchor assembly of claim 3, wherein the insertion tool further comprises a spool for storing excess suture material.

5. The suture anchor assembly of claim 3, wherein the insertion tool comprises an insertion tool first end and an insertion tool second end, the insertion tool first end including a handle and the insertion tool second end including an elongated body configured to insert the suture anchor assembly into the pilot hole.

6. The suture anchor assembly of claim 5, wherein the insertion tool second end comprises a flat end or a rounded end.

7. The suture anchor assembly of claim 5, wherein the insertion tool second end comprises an anchor slot for receiving at least a portion of the suture anchor assembly.

8. The suture anchor assembly of claim 4, wherein the insertion tool further comprises one or more eyelets positioned along a length of the elongated body.

9. The suture anchor assembly of claim 8, wherein the one or more eyelets include a plurality of eyelets that are positioned at one or more predetermined lengths from the insertion tool second end to allow a surgeon to insert the suture anchor assembly at a controlled depth.

10. The suture anchor assembly of claim 1, further comprising a drill for drilling a pilot hole into a bone.

11. The suture anchor assembly of claim 1, wherein one or more of the first deployment strand, the second deployment strand, and the sleeve are comprised of a material infused with osteoconductive material.

12. A method of attaching a suture anchor assembly to a bone, comprising:

drilling a pilot hole into the bone using a drill;

inserting an anchor into the pilot hole via an insertion tool, the anchor comprising:

a sleeve having an elongated configuration and a tightened configuration;

10 a first deployment strand and a second deployment strand, each of the first deployment strand and the second deployment strand forming a looped end and a free end, wherein:

the free end of the first deployment strand passes through the looped end of the second deployment strand and the free end of the second deployment strand passes through the looped end of the first deployment strand, thereby forming a loose square knot with a first crossover and a second crossover; and a portion of the first deployment strand and a portion of the second deployment strand pass through the sleeve;

deploying the anchor by tensioning the free end of the first deployment strand and the free end of the second deployment strand, thereby tightening the square knot and causing the sleeve to move to the tightened configuration; and removing the insertion tool from the pilot hole.

13. The method of claim 12, wherein the first crossover comprises the portion of the first deployment strand and the portion of the second deployment strand that passes through the sleeve.

14. The method of claim 12, wherein one or more of the first deployment strand, the second deployment strand, and the sleeve are comprised of a material infused with osteoconductive material.

15. The method of claim 12, further comprising inserting the suture anchor assembly into an anchor slot of the insertion tool.

16. The method of claim 12, further comprising storing excess suture in a spool of the insertion tool.

17. The method of claim 12, further comprising inserting the suture anchor assembly into one or more eyelets of an elongated body of the insertion tool.

18. The method of claim 17, wherein the suture anchor assembly is inserted into a predetermined eyelet at a predetermined length from an end of the insertion tool to control an insertion depth.

19. A kit for attaching a suture anchor assembly to a bone, comprising:

a drill configured to drill a pilot hole into the bone;

an insertion tool configured to insert a suture anchor assembly into the pilot hole; and the suture anchor assembly comprising:

a sleeve including an elongated configuration and a tightened configuration;

a first deployment strand and a second deployment strand, each of the first deployment strand and the second deployment strand forming a looped end and a free end, wherein:

the free end of the first deployment strand passes through the looped end of the second deployment strand and the free end of the second deployment strand passes through the looped end of the first deployment strand, thereby forming a loose square knot with a first crossover and a second crossover;

a portion of the first deployment strand and a portion of the second deployment strand pass through the sleeve; and application of tension to each of the free end of the first deployment strand and the free end of the second deployment strand causes the loose square knot to tighten and the sleeve to move to the tightened configuration.

20. The kit of claim 19, wherein the suture anchor assembly is loaded onto the insertion tool via an anchor slot.

\* \* \* \* \*